United States Patent
Fredman et al.

(10) Patent No.: US 6,492,337 B1
(45) Date of Patent: Dec. 10, 2002

(54) GALACTOSYLCERAMIDE, GLUCOSYLCERAMIDE, LACTOSYLCERAMIDE, AND SPECIFIC CATCHERS THEREFOR FOR USE IN THE PROPHYLAXIS OR THERAPY OF PREDIABETES, DIABETES AND/OR ASSOCIATED COMPLICATION

(75) Inventors: Pam Fredman, Göteborg (SE); Karsten Buschard, Charlottenlund (DK)

(73) Assignee: A+ Science AB, Göteborg (SE)

( * ) Notice: Subject to any disclaimer, the term of this patent is extended or adjusted under 35 U.S.C. 154(b) by 0 days.

(21) Appl. No.: 09/582,656

(22) PCT Filed: Dec. 21, 1998

(86) PCT No.: PCT/SE98/02407

§ 371 (c)(1),
(2), (4) Date: Sep. 21, 2000

(87) PCT Pub. No.: WO99/33475

PCT Pub. Date: Jul. 8, 1999

(30) Foreign Application Priority Data

Dec. 30, 1997 (DK) .............................................. 1553/97

(51) Int. Cl.[7] ...................... A01N 43/04; A61K 37/715; C07K 16/00; C12P 21/08; C07H 15/00
(52) U.S. Cl. .............................. 514/25; 514/53; 514/54; 514/866; 530/387.2; 530/387.5; 530/388.1; 530/389.1; 536/17.6
(58) Field of Search ............................ 514/25, 53, 54, 514/866; 530/387.2, 387.5, 388.1, 389.1; 536/17.6

(56) References Cited

U.S. PATENT DOCUMENTS 5,242,800 A    9/1993  Jimenez et al. .............. 435/7.2
5,827,828 A  * 10/1998  Buschard et al. ............. 514/25

FOREIGN PATENT DOCUMENTS

EP    0133170       2/1985
EP    0579196       1/1994
WO    WO 92/19633   11/1992
WO    WO 97/42974   11/1997

OTHER PUBLICATIONS

APMIS, vol. 104, pp. 938 to 944 (1996).
STN International, File Medline, Medline Accession No. 97032815, Document No. 97032815, M.A. Sosa et al.
Buschard et al., "Sulfatide and Galactosylceramide Regulates the Production of IL–6 from Huma Lymphocytes", *Acta Pathologica, Microbiologica et Immunologica Scandinovica (APMIS)*, pp. 941–944, Blackwell Munkagaard, Copenhagen, Denmark.

* cited by examiner

*Primary Examiner*—Jeffrey J Fredman
*Assistant Examiner*—Arun kr. Chakrabarti
(74) *Attorney, Agent, or Firm*—Burns, Doane, Swecker & Mathis, LLP

(57) ABSTRACT

The use of glycolipids, in particular galactosylceramide, glucosylceramide and lactosylceramide, and specific catchers therefor (antibodies or lectins), in particular monoclonal antibodies, for use in the prophylaxis or therapy of prediabetes, diabetes and/or associated complications in an individual and for use in the production of pharmaceutical preparations for treatment of said conditions is disclosed.

6 Claims, No Drawings

GALACTOSYLCERAMIDE, GLUCOSYLCERAMIDE, LACTOSYLCERAMIDE, AND SPECIFIC CATCHERS THEREFOR FOR USE IN THE PROPHYLAXIS OR THERAPY OF PREDIABETES, DIABETES AND/OR ASSOCIATED COMPLICATION

TECHNICAL FIELD OF THE INVENTION

The present invention relates to the use of glycolipids and specific catchers therefore in treatment of diabetes.

BACKGROUND OF THE INVENTION

Galactosylceramide is a glycolipid consisting of ceramide to which galactose is attached. It is made by the enzyme ceramide galactosyltransferase which binds its two parts together. Galactosylceramide is a precursor of sulfatide and is present in the neural system and in islets of Langerhans in small amounts. A sulfatransferase enzyme is able to attach sulfate to the galactose group and thereby to convert galactosylceramide to sulfatide. It is a possibility that galactosylceramide given in vivo is converted to sulfatide. However, galactosylceramide may also act by itself and, indeed effects of galactosylceramide have been described in vitro (Buschard, K., Diamant, M., Bovin, L. F., Fredman, P., Bendtzen, K., Sulphatide and its precursor, galactosylceramide, influence the production of cytokines in human mononuclear cells. APMIS 104: 938–944, 1996). It has been shown that galactosylceramide can modulate and mainly enhance the production of different cytokines from both monocytes and T-cells after stimulation with LPS and PHA, respectively.

Most importantly TNF and IL-6 production is increased compared to incubation with LPS and PHA without galactosylceramide.

Glucosylceramide and lactosylceramide are related glycolipids which likely have the same effects as galactosylceramide.

SUMMARY OF THE INVENTION

The present invention relates to the use of a glycolipid or a specific catcher thereof for the production of a pharmaceutical preparation for treatment of prediabetes, diabetes and/or associated complications in an individual.

Furthermore, the invention relates to glycolipids, in particular galactosylceramide, glucosylceramide and lactosylceramide, and specific catchers therefore (antibodies or lectins) for use in the prophylaxis or therapy of prediabetes, diabetes and/or associated complications in an individual.

The invention also relates to a specific catcher for the glycolipids according to the invention, said catcher being a monoclonal antibody against galactosylceramide, glucosylceramide or lactosylceramide.

The invention also relates to a method for preventing the development of prediabetes, diabetes and/or associated complications in an individual, wherein a glycolipid, in particular galactosylceramide, glucosylceramide or lactosylceramide, is administered to said individual, preferably at its perinatal stage.

The characterising features or the invention will be evident from the following description and the appended claims.

DETAILED DESCRIPTION OF THE INVENTION

As stated above, the invention relates glycolipids, in particular galactosylceramide, glucosylceramide and lactosylceramide, and specific catchers therefore (antibodies or lectins) for use in the prophylaxis or therapy of prediabetes, diabetes and/or associated complications in an individual, as well as to the use of a glycolipid or a specific catcher thereof for the production of a pharmaceutical preparation for treatment of prediabetes, diabetes and/or associated complications in an individual.

The expression "treatment" used herein relates to both the prophylaxis of said conditions in an individual being in risk of developing any of the conditions and to the therapeutic treatment of an individual who have already developed any of the conditions.

The prophylactic treatment is performed by inducing tolerance to the antigenic glycolipids. When the glycolipids, the specific catchers therefore and/or the pharmaceutical preparation according to the invention is used for this purpose they are preferably administered perinatally to said individual.

The glycolipid used according to the invention is preferably galactosylceramide, glucosylceramide or lactosylceramide. The specific catcher used according to the invention is preferably an antibody or a lectin, and more preferably a monoclonal antibody against galactosylceramide, glucosylceramide or lactosylceramide.

The glycolipid, the specific catcher or the pharmaceutical preparation according to the invention may be administered in any suitable way known to the man skilled in the art. Preferably, they are administered nasally, orally, subcutaneously, intramuscularly, or intravenously.

The glycolipids or the pharmaceutical preparation may lead to increased levels of suppressor or regulator cells or antibodies against lymphocytes recognising the antigenic glycolipids in said individual. Alternatively, they may lead to the removal of antibodies and/or lymphocytes recognising the antigenic glycolipids from the blood stream of the individual.

It may be suitable to administer the glycolipids according to the invention together with bacterial adjuvants. The pharmaceutical composition according to the invention may therefore also comprises a least one bacterial adjuvant, such as cholera, staphyloccoc or galactosylceramide (alpha-form) of bacterial origin.

The pharmaceutical preparation according to the invention may also comprise substances used to facilitate the production of the pharmaceutical preparation or the administration of the preparations. Such substances are well known to people skilled in the art and may for example be pharmaceutically acceptable adjuvants, carriers and preservatives.

When antibodies are used according to the invention they will lead to an increase of anti-antibodies in said individual.

The invention also relates to a method for preventing the development of prediabetes, diabetes and/or associated complications in an individual, wherein a glycolipid, in particular galactosylceramide, glucosylceramide or lactosylceramide, is administered to said individual, preferably at its perinatal stage.

The method may be performed by removing lymphocytes from the individual, contact the lymphocytes with a glycolipid, in particular galactosylceramide, glucosylceramide or lactosylceramide, in vitro to make them recognise this antigen, irradiating them to inhibit their cytotoxicity, and (a) returning them to the individual to raise suppressor or regulator cells or antibodies against lymphocytes reactive with this antigen, or (b) administering them parenterally to another mammal in order to raise antibodies against lymphocytes reactive with this antigen in said mammal and then isolating serum containing the antibodies from said mammal and administering it to the individual.

The method may also be performed by contacting the blood stream of the individual with an immobilised glycolipid, in particular galactosylceramide, glucosylceramide or lactosylceramide, to remove antibodies and/or lymphocytes recognising the antigenic glycolipids from the individual.

Finally, it is also possible to perform the method by parenterally administer an antibody against glycolipids, in particular galactosylceramide, glucosylceramide or lactosylceramide, (a) to said individual in a sufficient amount to raise anti-antibodies in said individual, or (b) to another mammal in order to raise anti-antibodies in said mammal and then isolating serum containing the anti-antibodies from said mammal and administering it to the individual.

The invention will now be further explained in the following example. This example is only intended to illustrate the invention and should in no way be considered to limit the scope of the invention.

EXAMPLE

Treatment of NOD Mice with the Intrathymic Injections of Galactosylceramide in Order to Modulate the Later Diabetes Incidence Materials and methods The NOD mouse model is an animal model of type 1 diabetes. The mice develop spontaneously diabetes within 200 days of life with an incidence of 50% or more. In the present study the animals were examined daily and once a week checked for glucosuria. They were diagnosed as diabetic if their blood glucose values was higher than 200 mg glucose per 100 ml. When diagnosed as diabetics the animals were sacrificed. Otherwise the remaining non-diabetic animals were sacrificed at the end 5 of the study after 200 days of age.

Four groups of animals each containing between 30 and 40 animals were investigated: The animals were injected intrathymically when 3 weeks old. There was injected 50 µl galactosylceramide in 100 µl vehicle (PBS). The control mice were treated with the 100 µl PBS alone. In another experiment liposome preparation of galactosylceramide was made using phosphatidylcholin and galactosylceramide. The control group was treated with phosphatidylcholin and PBS alone.

Results

In the first study with treatment of galactosylceramide in pure form 17 of 37 mice (=45.9%) developed diabetes, whereas 21 of 37 (=56.8%) of the control (PBS-treated) mice developed the disease. In the second study with galactosylceramide in liposome form 14 of 33 (=42.4%) of the galactosylceramide liposome treated mice developed diabetes whereas 18 of 31 (=58.1%) of the control (PBS-treated) mice develop the disease.

Taking the two studies together 31 of 70 (=44.3%) of the galactosylceramide treated mice developed diabetes whereas 39 of 68 (=57.4%) of PBS mice developed the disease. In the first study the diabetes development in the galactosylceramide treated group occurred later than among the control mice.

What is claimed is:

1. A method for preventing the development of prediabetes, diabetes and/or associated complications in an individual, wherein an effective amount of non-sulfated galactosylceramide is administered to said individual in need of such prevention.

2. A method for preventing or treating prediabetes, diabetes and/or associated complications in an individual, wherein lymphocytes are removed from the individual, contacted with an effective amount of non-sulfated galactosylceramide in vitro to make them recognize the antigen, irradiating the lymphocytes to inhibit their cytotoxicity, and (a) returning them to the individual to raise suppressor or regulator cells or antibodies against lymphocytes reactive with the antigen, or (b) administering them parenterally to another mammal in order to raise antibodies against lymphocytes reactive with this antigen in said mammal and then isolating serum containing the antibodies from said mammal and administering it to the individual.

3. A method for preventing or treating prediabetes, diabetes and/or associated complications in an individual, wherein the blood stream of the individual is contacted with an effective amount of immobilised non-sulfated galactosylceramide to remove antibodies and/or lymphocytes recognizing the antigenic glycolipids from the individual.

4. A method of preventing or treating prediabetes, diabetes and/or associated complications in an individual, wherein an effective amount of an antibody against non-sulfated galactosylceramide is parenterally administered (a) to said individual in a sufficient amount to raise anti-antibodies in said individual, or (b) to another mammal in order to raise anti-antibodies in said mammal and then isolating serum containing the anti-antibodies from said mammal and administering it to the individual.

5. The method according to claim 2, wherein said glycolipid is administered manually, orally, subcutaneously, intramuscularly, or intravenously.

6. The method according to claim 2, wherein said galactosylceramide is administered perinatally.

* * * * *